United States Patent [19]

Howard

[11] Patent Number: 5,021,049
[45] Date of Patent: Jun. 4, 1991

[54] NEEDLE SHEATH HOLDER WITH SEEPAGE PRECLUDING ENGAGEMENT ZONES

[76] Inventor: Richard S. Howard, 6737 Locust, Kansas City, Mo. 64131

[21] Appl. No.: 484,889

[22] Filed: Feb. 26, 1990

[51] Int. Cl.$^5$ .............................................. A61M 5/32
[52] U.S. Cl. .................................. 604/192; 604/263; 206/365
[58] Field of Search ................ 206/365, 367; 604/192, 604/194, 197, 263, 110, 111, 198

[56] References Cited

U.S. PATENT DOCUMENTS

| | | | |
|---|---|---|---|
| 3,021,942 | 2/1962 | Hamilton | 206/365 |
| 3,245,567 | 4/1966 | Knight | 604/263 X |
| 3,333,682 | 8/1967 | Burke | 206/365 |
| 3,367,488 | 2/1968 | Hamilton | 206/365 |
| 3,796,359 | 3/1974 | Dick . | |
| 4,106,622 | 8/1978 | Windischman | 206/365 |
| 4,332,323 | 6/1982 | Reenstierna . | |
| 4,375,849 | 3/1983 | Hanifl . | |
| 4,485,918 | 12/1984 | Mayer . | |
| 4,576,281 | 3/1986 | Kirksey . | |
| 4,623,336 | 11/1986 | Pedicano et al. | 604/192 |
| 4,654,034 | 3/1987 | Masters et al. | 604/192 |
| 4,664,259 | 5/1987 | Landis . | |
| 4,715,498 | 12/1987 | Hanifl . | |
| 4,738,362 | 4/1988 | Burns et al. . | |
| 4,740,204 | 4/1988 | Masters et al. | 604/192 |
| 4,742,910 | 5/1988 | Staebler . | |
| 4,758,231 | 7/1988 | Haber et al. | 604/263 X |
| 4,799,927 | 1/1989 | Davis et al. | 604/192 |
| 4,802,579 | 2/1989 | Hall et al. . | |
| 4,804,090 | 2/1989 | Schuh et al. . | |
| 4,809,850 | 3/1989 | Laible et al. . | |
| 4,871,355 | 10/1989 | Kikkawa | 604/198 |
| 4,892,525 | 1/1990 | Hermann, Jr. et al. | 604/263 |

FOREIGN PATENT DOCUMENTS

| | | | |
|---|---|---|---|
| 253426 | 5/1963 | Australia | 206/365 |
| WO8503006 | 7/1985 | PCT Int'l Appl. | 604/192 |

OTHER PUBLICATIONS

Article from "New England Journal of Medicine" 319:284-288 (Aug. 4, 1988).

Primary Examiner—Bryon P. Gehman
Attorney, Agent, or Firm—Michael Yakimo, Jr.

[57] ABSTRACT

A sheath for a medical needle device such as a syringe or blood collection device comprises a barrel, hub, cone and shield. The needle device is guided into a visible aperture surrounded by the shield at the top of the cone for ultimate extension of the needle through the hub and into the barrel. The sheath precludes splashing of body fluids onto the user upon capping as well as accidental puncture. The barrel, hub and cone elements of the sheath provide a plurality of friction-fit engagements with the medical needle device to preclude accidental decapping and seepage of fluids from the sheathed needle and onto the user.

8 Claims, 1 Drawing Sheet

NEEDLE SHEATH HOLDER WITH SEEPAGE PRECLUDING ENGAGEMENT ZONES

BACKGROUND OF THE INVENTION

This invention relates to improvements in devices for safely disposing of used medical needles, and more particularly, to devices which allow for a simple, safe, permanent and cost-effective resheathing of a used medical needle.

Subsequent to withdrawal of a needle from a patient, the tip of a needle, whether associated with a drug injection or fluid collection device, may carry body fluids of the patient. Such a body fluid may be transmitted to the medical user by splashing onto the skin or accidental puncture of the user's skin by the needle. Such transmission may communicate an undesirable disease, associated with the body fluid, to the needle user. The term "user" comprises a medical technician, nurse, doctor, etc.

The occurrences of needle-stick injuries caused by various devices in a university hospital is a significant problem in the medical art. An article in the *New England Journal of Medicine*, 319:284-288 (Aug. 4, 1988) identifies various characteristics of devices that caused needle-stick injuries in a university hospital over a ten-month period. Of the 326 injuries studied over a ten-month period, it was found that disposable syringes accounted for 35%, intravenous tubing and needle assemblies for 26%, pre-filled cartridge syringes for 12%, winged steel-needle intravenous sets for 7%, phlebotomy needles for 5%, intravenous catheters stylists for 2% and other devices for 13%. The study found that one-third of the needle puncture injuries were related to recapping of a used needle.

The recapping incidents were found to occur in three ways:
1. The needle user missed the original needle cap which caused the needle to stick in the opposing hand of the user;
2. The needle pierced the needle cap during recapping;
3. The cap fell off a recapped needle.

As to this latter problem, a hazard remains after a cap is replaced, because of a variability in the friction fit securing the cap to the needle hub. Accordingly, it is apparent that there is a need in the medical area for effective needle recapping devices. Although various devices have been suggested to address this need, they are relatively complex in structure and use and may not be effective in a medical environment. Moreover, they do not appear to address the safety aspects of recapping the needle and holding the cap in place.

In response thereto, I have developed a needle sheath which easily and safely guides a used medical needle assembly therein and offers a positive friction fit between the needle sheath and needle assembly so as to preclude any undesirable needle puncture and decapping. My holder presents an elongated barrel for enclosing the used needle; an integral hub element for enclosing the hub or base of the needle assembly; an integral cone element for enclosing the distal portion of the fluid collection cylinder of the needle assembly and an integral shield at the top end therein for enclosing a distal portion of the fluid collection tube and for protecting the opposite hand of the user. The shield and cone elements present sloping walls so as to guide the needle into successively downstream elements and ultimately into the barrel so as to preclude undesirable puncture of the needle through the sheath. Concurrently, the various integral elements provide a plurality of friction fits of the holder with the needle assembly to preclude the sheath from falling off the needle subsequent to capping. Accordingly, my device addresses the three problems set forth in the above-identified article.

It is therefore a general object of this invention to provide a sheath for safely enclosing a used medical needle assembly.

Another object of this invention is to provide a sheath, as aforesaid, which safely guides a used medical needle into a protective enclosure.

A still further object of this invention is to provide a sheath, as aforesaid, which encompasses portions of the accompanying needle assembly so as to enhance the recapping of the used needle and preclude undesirable splashing of body fluids.

A more particular object of this invention is to provide a sheath, as aforesaid, which presents structure for providing a plurality of friction fits with the needle assembly.

Other objects and advantages of this invention will become apparent from the following description taken in connection with the accompanying drawings, wherein is set forth by way of illustration and example, an embodiment of this invention.

DESCRIPTION OF THE PREFERRED EMBODIMENT

Figure 1:
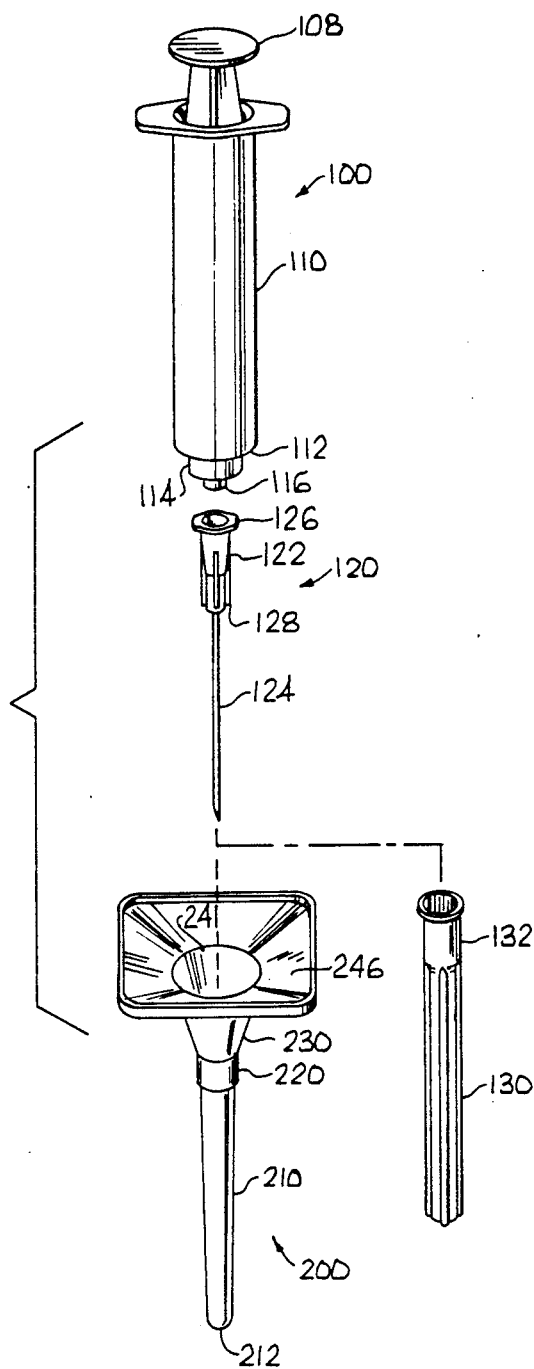
FIG. 1 illustrates one type of medical needle assembly, in actual scale, for use with my novel needle sheath with the original needle cap being shown at one side thereof
Figure 2:
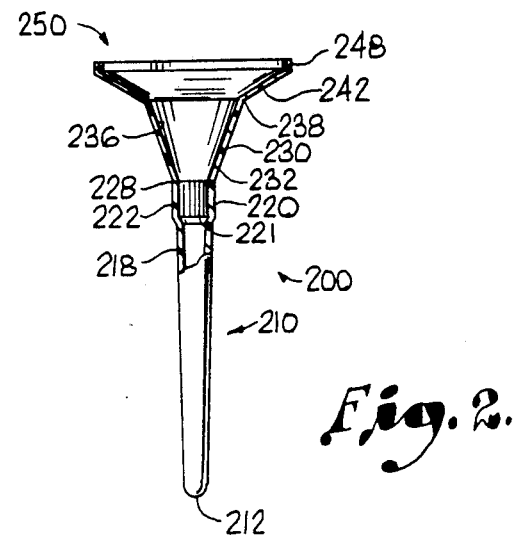
FIG. 2 illustrates a partial, central sectional view of the sheath in FIG. 1 so as to illustrate the interior of the integral barrel, cone, hub and shield elements comprising the needle sheath.
Figure 3:
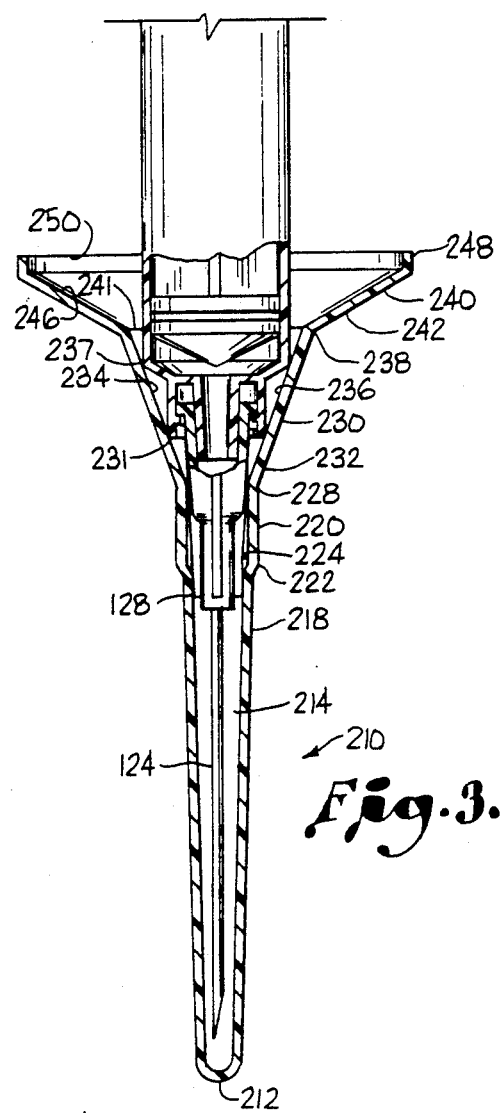
FIG. 3 is a central sectional view, on an enlarged scale, illustrating the needle assembly of FIG. 1 capped in the novel needle sheath.

Turning more particularly to the drawings, FIG. 1 illustrates one type of medical needle assembly in the form of a syringe-like device 100. It is understood that my device 200 can be used with various medical needle assemblies such as blood collection devices, syringes and the like and should not be limited to this illustrated needle assembly 100.

As such, the syringe 100 comprises a generally cylindrical fluid collection tube 110 having a reciprocal plunger 108 slidably mounted therein. Extending from the bottom 112 of the fluid collection tube 110 is a cylindrical boss 114 encompassing a spigot 116. The spigot 116 includes a central interior bore in communication with the interior of the fluid collection tube 110.

The needle assembly 120 comprises a hub 122 with a plurality of vertical flanges 128 therearound. Extending from the hub 122 is a medical needle 124 with interior bore for fluid communication therethrough. The interior surfaces of the hub 122 engage the exterior surfaces of the spigot 116 in a friction fit therebetween. Concurrently, the boss 114 interior engages the edges of the upper flange 126 of the hub 122 in a friction fit therebetween. As such, the needle 124 communicates with the fluid collection tube 110 via the hub 122 and spigot 116.

Subsequent to use the needle 124 and/or lower portions of tube 110 may contain body fluids within and without its bore which may be accidentally transmitted to the needle user either by splashing or accidental skin puncture.

As shown in FIG. 1, the conventional cap 130 includes a hub 132 which fits about the hub 122 in a friction fit therebetween. As above described, recapping of the used needle 124 with this conventional cap 130 may result in accidental puncture to the hand of the user upon an attempted insertion of the needle 124 into the interior of this conventional cap 130. Also, the needle 124 may pierce the cap 130 during recapping if a shorter cap from another needle assembly is accidentally used. Finally, the conventional cap 130 may fall off subsequent to capping which exposes the needle 124 and accompanying fluids to the user.

To alleviate such problems, I provide a novel sheath 200 which comprises a plurality of integral elements having a plurality of friction-fit engagements with the needle assembly 100 and encompasses the lower portions of tube 110 which may contain body fluids thereon. The sheath 200 comprises from the distal end 212 to the proximal end 248 successive integral elements commencing at the distal end 212 with an elongated barrel 210 having a hollow needle-receiving bore 214 with closed distal end 212 therein. The bore 214 at the proximal end 218 of barrel 210 engages the flanges 128 of the hub 122 in a friction-fit engagement therebetween.

Extending from the proximal end 218 of barrel 210 is an integral hub element 220 having distal 222 and proximal 228 ends with a central bore 224 therein. The cross section of the proximal end 228 of hub 220 allows for projection of a portion of the needle hub 122 therein. The cross section of the hub bore 224 at proximal end 228 is preferably greater than the bore 214 opening at the distal end 212 of the barrel 210. Upon such projection, the interior knurled surface 221 of the bore 224 at the proximal end 228 engages a portion of the hub 122 or its flanges 128 in a friction fit engagement therewith. This hub 122 engagement with hub 220 of sheath 200 also provides a seal to preclude seepage of fluids from the barrel 210 upon recapping.

Extending from the proximal end 228 of hub 220 is a cone 230 with a converging bore 234. The cone 230 has distal 232 and proximal 238 ends with sloping walls 236 extending therebetween. The proximal end 238 of cone 230 bore 234 presents an aperture 241 visible to the user. Aperture 241 has a cross section allowing for extension of needle assembly 120 and a portion of the distal end 112 of the fluid collection tube 110 therethrough. The sloping walls 236 present subsequent points of friction-fit engagement between the sheath 200 and portions of the medical device 100 (231, 237 as shown). These annular zones of engagement further provide a seal to preclude seepage of fluids from barrel 210.

Upwardly extending from the proximal end 238 of cone 230 is a shield 240 having proximal 248 and distal 24 ends. Shield 240 presents converging walls 246 extending between said proximal 248 and distal 242 ends. The shield 240 presents a proximal opening 250 which is larger than the diameter of the fluid collection tube 110 and visible aperture 240. Accordingly, each aperture at the proximal end of each respective bore is greater than the opening of the respective downstream bore.

In use, subsequent to needle 124 withdrawal from the patient, the sheath 200 is held in one hand with the syringe 100 in the other. Upon needle 124/sheath 200 convergence, the needle 124 is easily guided into the visible aperture 241 as aided by the converging walls 246 of the shield 240. The shield further protects the hand of the user from splashing of body fluids thereon and/or needle puncture. The needle 124 is then extended through the respective bores in the cone elements 230, hub element 220 and barrel 210. As the various cross-sectional openings of the bores of the downstream integral elements are successively reduced, the needle 124 is guided into a capped position without the possibility of the needle puncturing any of these elements. Also as above described, the sheath 200 provides a number of frictional-fit engagements between the needle assembly 100 and sheath 200 about the hub 122 and collection tube 110 which not only provides tactile indicia to the user that the needle device 100 has been properly capped but also diminishes the probability of the sheath 200 falling from the needle 124 subsequent to capping. Moreover, the respective zones of friction-fit engagement provide a number of annular seals which preclude the undesirable seepage of fluids from the capped needle 124.

Although an embodiment of my sheath 200 has been hereinabove described, it is understood that it is not to be limited thereto except as set forth in the following claims and functional equivalents thereof.

Having thus described the invention, what is claimed as new and desired to be secured by Letters Patent is:

1. For use with a medical needle device having a needle assembly with a needle projecting from an end of a fluid collection tube, a sheath having a closed distal end and an open proximal end, comprising:
   an elongated barrel having a distal closed end and a proximal end for enclosing said needle and having a barrel bore with distal and proximal ends, said barrel bore extending between said distal and proximal ends of said barrel, said barrel bore having a cross section to provide a zone for engagement of said barrel bore with a portion of said needle assembly;
   a hub extending from the barrel proximal end for enclosing a portion of said needle assembly therein, said hub having a hub bore with a distal end, in communication with said proximal end of said barrel bore, and a proximal end, said hub bore having a cross section to provide a zone for annular engagement of a portion of said hub bore about a portion of said needle assembly, the zone of the annular engagement being displaced from the zone of the barrel bore engagement, the annular engagement precluding seepage of fluid between said hub and said portion of said needle assembly;
   a cone having a distal end and a proximal end and extending from the hub proximal end for receiving a portion of said collection tube therein, said cone having a converging cone extending through said cone with a distal end in communication with the hub bore proximal end, said cone bore guiding said needle into said hub and presenting a visible aperture at said proximal end of said cone;
   a shield with a proximal end and a distal end and extending from the cone proximal end and encompassing said visible aperture, said shield having a sloping wall between said proximal and distal ends for guiding said needle into said visible aperture of said cone through said hub and into said barrel.

2. The sheath as claimed in claim 1, wherein said cone bore has a cross section to provide for an annular engagement of said cone bore about a lower portion of said collection tube.

3. The sheath as claimed in claim 2, wherein annular engagement of said cone bore with said collection tube precludes seepage of fluid between said cone bore and said portion of said collection tube.

4. The sheath as claimed in claim 2, wherein said converging cone bore has a cross section to further provide an annular engagement of said cone bore about an upper portion of said collection tube at a zone displaced from said annular engagement of said cone bore with said lower portion of said collection tube.

5. The sheath as claimed in claim 1, wherein the barrel bore engagement provides an annular engagement about said needle assembly to preclude seepage of fluid between said needle assembly and said barrel.

6. For use with a medical needle device having a needle assembly with a needle projecting from an end of a fluid collection tube, a sheath, having a closed distal end and an open proximal end, comprising:
- an elongated barrel having a distal closed end and a proximal end for enclosing said needle and having a barrel bore with distal and proximal ends, said barrel bore extending between said distal and proximal ends of said barrel, said barrel bore having a cross section to provide a zone for engagement of said barrel bore with a portion of said needle assembly;
- a hub extending from the barrel proximal end for enclosing a portion of said needle assembly therein, said hub having a hub bore with a distal end, in communication with said proximal end of said barrel bore, and a proximal end, said hub bore having a cross section to provide a zone for engagement of a portion of said hub bore about a portion of said needle assembly, the zone of the hub bore engagement being displaced from the zone of the barrel bore engagement;
- a cone having a distal end and a proximal end and extending from the hub proximal end for receiving a portion of said collection tube therein, said cone having a converging cone bore extending through said cone with a distal end in communication with the hub bore proximal end, said cone bore guiding said needle into said hub and presenting a visible aperture at said proximal end of said cone, said cone bore having a cross-section to provide an annular engagement of a portion of said cone bore about a lower portion of said fluid collection tube to preclude seepage therebetween;
- a shield with a proximal end and a distal end and extending from the cone proximal end and encompassing said visible aperture, said shield having a sloping wall between said proximal and distal ends for guiding said needle into said visible aperture of said cone through said hub and into said barrel.

7. The sheath as claimed in claim 6, wherein said converging cone bore has a cross section to further provide an annular engagement of said cone bore about an upper portion of said collection tube at a zone displaced from the zone of the annular engagement of the portion of said cone bore about the lower portion said collection tube.

8. The sheath as claimed in claim 6, wherein engagement of said barrel bore with a portion of said needle assembly provide an annular engagement about said needle assembly to preclude seepage of fluid between said needle assembly and said barrel bore.

* * * * *

UNITED STATES PATENT AND TRADEMARK OFFICE
CERTIFICATE OF CORRECTION

PATENT NO. : 5,021,049
DATED : June 4, 1991
INVENTOR(S) : RICHARD S. HOWARD

It is certified that error appears in the above—identified patent and that said Letters Patent is hereby corrected as shown below:

Column 4, claim 1, line 58: after "cone" insert --bore--.

Column 6, claim 7, line 29: before the second occurrence of the word "said" insert --of--.

Signed and Sealed this

Twenty-seventh Day of October, 1992

Attest:

DOUGLAS B. COMER

Attesting Officer     Acting Commissioner of Patents and Trademarks